US00PP13053P2

(12) United States Plant Patent
Garabedian

(10) Patent No.: US PP13,053 P2
(45) Date of Patent: Oct. 8, 2002

(54) VARIETY OF APRICOT TREE NAMED 'ROSY BELL'

(76) Inventor: John M. Garabedian, deceased, late of Fresno, CA (US), by Malcolm H. Stewart, legal representative ( * ) Notice: Subject to any disclaimer, the term of this patent is extended or adjusted under 35 U.S.C. 154(b) by 0 days.

(21) Appl. No.: 09/595,537

(22) Filed: Jun. 16, 2000

Related U.S. Application Data

(63) Continuation of application No. 09/153,007, filed on Sep. 14, 1998, now abandoned.

(51) Int. Cl.[7] ..... A01H 5/00
(52) U.S. Cl. ..... Plt./186
(58) Field of Search ..... Plt./184, 186

(56) References Cited

U.S. PATENT DOCUMENTS

PP3,345 P * 5/1973 Garabedian ..... Plt./186

OTHER PUBLICATIONS

UPOV–ROM GTITM Computer Database, 2001/02, GTI JOUVE Retrieval Software, citations for 'Rosy Bell'.*

* cited by examiner

*Primary Examiner*—Bruce R. Campell
*Assistant Examiner*—Susan B. McCormick
(74) *Attorney, Agent, or Firm*—Fitzpatrick, Cella, Harper, & Scinto

(57) ABSTRACT

A new variety of apricot tree which matures in mid-May in the San Joaquin Valley of Central California with a golden yellow color with a light red blush that stores and ships well. This early apricot handles beter than other early varieties such as 'Casselbrite'.

1 Drawing Sheet

This application is a continuation of application Ser. No. 09/153,007, filed on Sep. 14, 1998, now abandoned.

BACKGROUND OF THE NEW VARIETY

The present invention relates to a new and distinct variety of apricot tree which will hereupon be denominated varietally as 'Rosy Bell' apricot tree and more particularly to an apricot tree which produces fruit which are mature for commercial harvesting and shipment May 17–21 in the San Joaquin Valley of Central California. This new variety is an open pollinated seedling from one of its possible parents—'Early Perfection' (unpatented), 'Tilton' (unpatented), 'Patterson' (unpatented), and other unnamed varieties. This new variety produces a medium size, semi-freestone fruit with a golden yellow thick skin with a light red blush.

ORIGIN AND ASEXUAL REPRODUCTION OF THE NEW VARIETY

The present variety, an open pollinated seedling, has been budded and/or grafted in Nemaguard rootstock on exisiting older apricot tree (variety unknown) in 1994 in an apricot orchard of seven acres located at 5841 B. King Canyon Road, Fresno, Calif. The invention has been examined and confirmed that all of its distinctive characteristics have been maintained in a successful generation of asexual propagation.

SUMMARY OF THE NEW VARIETY

The 'Rosy Bell' apricot tree is characterized by producing a medium size fruit with a golden yellow center and a light red blush over approximately 40% of the fruit, which is ripe for commercial harvest and shipment May 17–21 in the San Joaquin Valley of Central California. This new and novel variety is an open pollinated seedling of unknown parentage—possibly 'Early Perfection' (unpatented), 'Tilton' (unpatented), 'Patterson' (unpatented), and other unnamed varieties, from which it is distingushed by early maturity, uniform fruit production, distribution, size and shape.

BRIEF DESCRIPTION OF THE DRAWING

The drawing is a colored photograph showing mature fruit of the present invention with foliage, young twigs and cut fruit displaying the flesh, stone or pit, and the pit well. The upper and lower surfaces of the leaves along with terminal growth of the branches are illustrated.

DETAILED DESCRIPTION

Referring to more specific pomological details of this new and distinct variety of apricot tree, the following description has been observed under the ecological conditions prevailing at the orchard of origin which is located in Fresno in the San Joaquin Valley of Central California. All major color code designations are by reference to the Dictionary of Color by Maerz and Paul, first edition, 1930. Common color names are also occasionally used.

Tree:

*Varietal name.*—'Rosy Bell'.

*Botanical name.*—*Prunus armeniaca.*

*Size.*—Large — Approximately 15 feet in height and 12 feet spread.

*Vigor.*—Moderate — New growth in year 2001 was 2.5 to 3 feet.

*Form.*—Upright with open crotch, vase-like form, depending on pruning practices.

*Productivity.*—Very productive in 2001 — 500 24 lb. boxes/acre.

Trunk:

*Size*—Large — 30 inches in circumference, 20 inches above ground level.

*Texture.*—Rough with some vertical grooves in the bark.
*Color.*—Dull brown — Cowboy new brown and brussel brown (Pl. 15 C11).
*Lenticels.*—Numerous, small.

Branches:
*Size*—Large — 18 inches in circumference at 24 inches above crown (crotch).
*Color of mature branches.*—Burgundy (Pl. 56 E8) with angle approximately 47 degrees.
*Color of young, immature branches.*—Smooth, crescent green (Pl. 22 K6).

Leaves:
*Size.*—Medium.
*Form.*—Broadly cordate, leaf tip acuminate base.
*Length.*—5.5 to 7.5 cm (2⅛ to 2⅞ inches).
*Width.*—5.5 to 7 cm (2⅛ to 2.75 inches).
*Color.*—Upper surface — Near Polo green (Pl. 23 L9). Lower surface — Spinach green (Pl 22 K9).
*Marginal form.*—Mostly serrate with serration becoming more rounded at base of leaf.
*Leaf vein.*—Reddish at base of leaf — Rhododendron (Pl. 5 I6).
*Glands.*—0–4 usually 1–2 small globular near leaf base or at the top of petiole.
*Petiole.*—20 to 22 mm long (0.79 to 0.87 inch) — 2 mm wide (0.079 inch) — Color: Rhododendron (Pl. 54 I6).
*Stipules.*—None.

Flower buds:
*Number.*—In clusters up to five.
*Color.*—Green.
*Size.*—Small — Average diameter 4 mm (0.157 inch).

Flowers:
*Date of bloom.*—February 22, 25 to 28.
*Size.*—Small — 16 mm diameter (0.63 inch).
*Color.*—Pinkish white (Pl. 1 B7).
*Petals.*—5.
*Pistil.*—1.
*Stamens.*—18–24 — Anthers — Very small — Color — Golden glow (Pl. 19 L6).
*Calyx.*—Piridine Green (Pl. 17 I6).

Fruit:
*Size.*—Medium compared to other apricot varieties.
*Average weight of fruit.*—5 to 10 apricots per pound.
*Average diameter.*—1.625 inch (41.28 mm).
*Transverse in the suture plane.*—1.59 inch (40.39 mm).
*Transverse at right angles to suture plane.*—1.71 inch (43.43 mm).
*Form.*—Roundish — Globose to slightly oblong.
*Suture.*—Distinct but shallow, occurring from apex to stem cup.
*Ventral surface.*—Smooth, rounded with some lips on dorsal side.
*Stem cavity.*—Average ⅝ inch deep (0.625 inch).
*Stem.*—Short — Length 0.5 inch (12.7 mm) — Caliper — 6.35 mm.
*Apex.*—Somewhat rounded to slightly truncated.
*Skin.*—Thin.
*Texture.*—Meaty.
*Tendency to crack.*—None known.
*Color.*—Blush — Light red average 40–45% of the fruit (4G5) — Ground color — Forsythia (9K6) — Flesh color — Cavity (Pl. L8) — Surface of pit well — Smooth, marabelle (Pl. 10 J9).
*Pit well.*—Length — 27 mm (1.06 inch) — Width — 18 mm (0.71 inch) — Color of pit well — Mirabelle (Pl. 10 J7).
*Juice production.*—Minimal.
*Flavor.*—Moderate to good.
*Aroma.*—Lacking.
*Texture.*—Meaty.
*Fibers.*—Few.
*Ripening.*—Even.
*Eating quality.*—Moderate to good.
*Keeping quality.*—Good.
*Shipping quality.*—Good.

Stone:
*Color.*—Dry Syrup (Pl. 14 L8).
*Type.*—Semi-free stone.
*Fibers.*—Few and short.
*Size.*—Length — 25 mm (0.98 inch) — Width — 17 mm (0.67 inch) — Thickness — 11 mm (0.43 inch).
*Form.*—General ovate.
*Hilum.*—Small, oval size.
*Apex.*—Somewhat rounded.
*Sides.*—Ventral side thin, while ridges from apex to base on dorsal side.
*Surface texture.*—Fine grooves at base.

Disease susceptibility/resistance: Similar to that of other varieties of apricots as it relates to brown rot and green fruit rot. A tendency to display reddish blemishes on the fruit when foggy conditions occur prior to harvest.

I claim:

1. A new and distinct variety of apricot tree named 'Rosy Bell' substantially as described and illustrated.

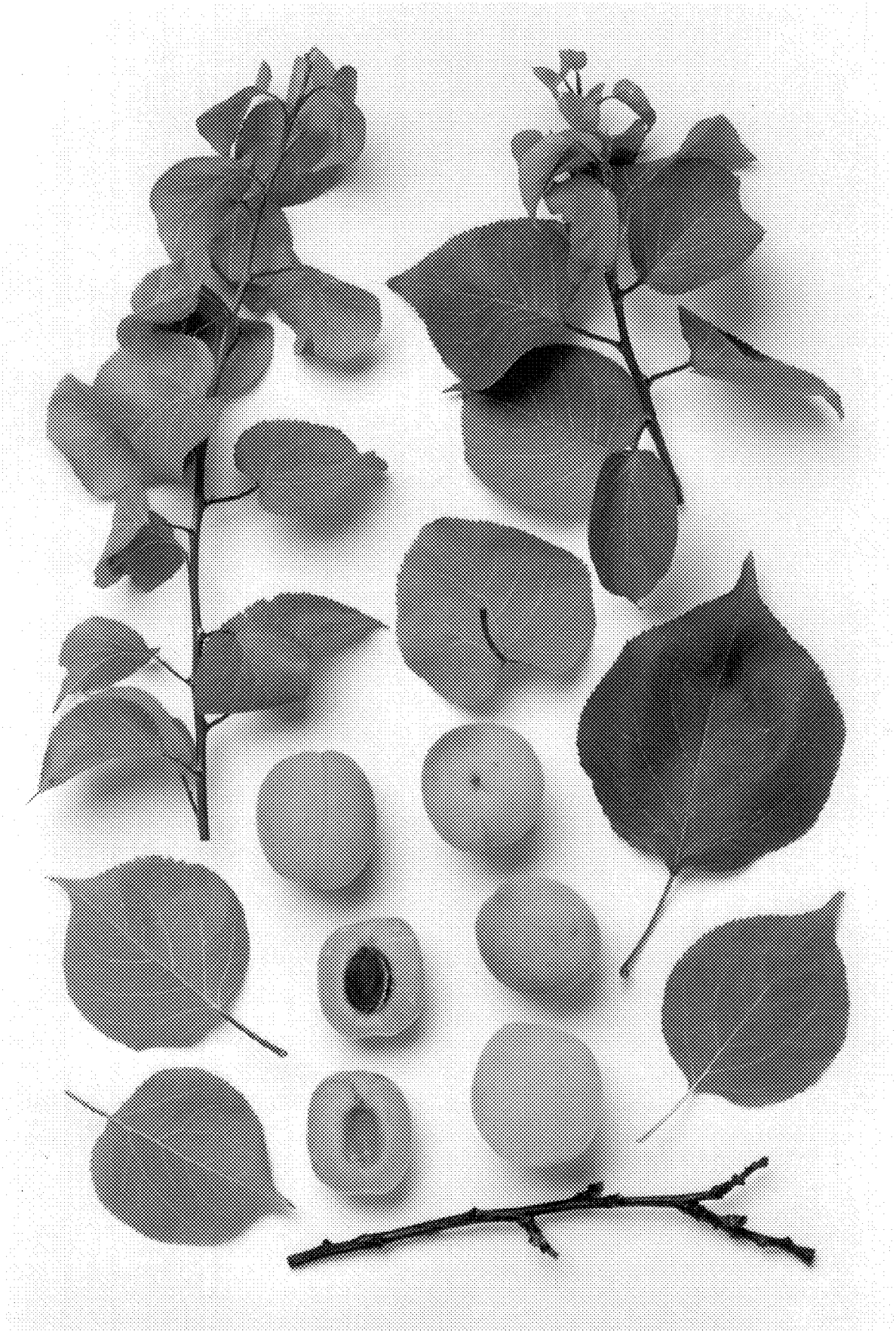

* * * * *